(12) United States Patent
Klots et al.

(10) Patent No.: US 8,336,481 B2
(45) Date of Patent: Dec. 25, 2012

(54) PRINTED INDICATOR COMPOSITIONS

(75) Inventors: Timothy D. Klots, Plymouth, MI (US); David D. Schatz, Ann Arbor, MI (US); Marc Schroeder, Canton, MI (US); Jürgen Kaczun, Wachenheim (DE)

(73) Assignee: BASF Corporation, Wyandotte, MI (US)

( * ) Notice: Subject to any disclaimer, the term of this patent is extended or adjusted under 35 U.S.C. 154(b) by 539 days.

(21) Appl. No.: 12/454,174

(22) Filed: May 13, 2009

(65) Prior Publication Data

US 2010/0288182 A1 Nov. 18, 2010

(51) Int. Cl.
*G01D 21/00* (2006.01)

(52) U.S. Cl. ............ 116/200; 116/206; 427/331

(58) Field of Classification Search ............ 116/200, 116/206–207, 216; 503/207; 427/331, 372.2; 106/472, 436, 481, 489; 283/61, 62, 67, 283/72, 95–97, 114, 901
See application file for complete search history.

(56) References Cited

U.S. PATENT DOCUMENTS

| | | | |
|---|---|---|---|
| 3,967,034 A * | 6/1976 | Meadus et al. ............ | 428/323 |
| 3,968,319 A | 7/1976 | Mani et al. | |
| 4,089,800 A | 5/1978 | Temple | |
| 4,972,000 A | 11/1990 | Kawashima et al. | |
| 5,106,813 A | 4/1992 | Hoshino et al. | |
| 5,256,619 A * | 10/1993 | Yoshida et al. ............ | 503/226 |
| 5,340,495 A | 8/1994 | Mulcahy et al. | |
| 5,585,321 A * | 12/1996 | Breen et al. ............ | 503/226 |
| 5,683,500 A | 11/1997 | Kawasumi et al. | |
| 6,063,849 A | 5/2000 | Morris et al. | |
| 7,185,601 B2 | 3/2007 | Carpenter et al. | |
| 7,704,667 B2 * | 4/2010 | Cheon et al. ............ | 430/235 |
| 7,717,992 B2 * | 5/2010 | Klots et al. ............ | 106/31.65 |
| 2007/0081115 A1 * | 4/2007 | Wada et al. ............ | 349/96 |
| 2010/0098843 A1 * | 4/2010 | Klots et al. ............ | 427/145 |

FOREIGN PATENT DOCUMENTS

| | | |
|---|---|---|
| JP | 2000-267358 A | 9/2000 |
| JP | 2002-30113 | 1/2002 |
| JP | 2006-053201 A | 2/2006 |

OTHER PUBLICATIONS

International Search Report and Written Opinion; PCT International Patent Application No. PCT/US2010/034483; Applicant: BASF Corporation, et al.; Mailed: Jan. 28, 2011, (8 pgs.).
*Polymer Handbook*, Third edition, Brandrup and Immergut, eds., John Wiley and Sons, New York, 1989, Ch. VI, pp. 213-258.
*Polymer Handbook*, Third edition, Brandrup and Immergut, eds., John Wiley and Sons, New York, 1989, Ch. VI, pp. 451-461.
International Preliminary Report on Patentability issued in PCT/US2010/034483 and mailed Nov. 24, 2011.

* cited by examiner

*Primary Examiner* — R. A. Smith
*Assistant Examiner* — Tania Courson
(74) *Attorney, Agent, or Firm* — Foley & Lardner LLP

(57) ABSTRACT

A method of revealing exposure of a substrate to an environmental stimulus includes exposing the substrate to the environmental stimulus, where the substrate includes at least one indicia, where each of the at least one indicia includes a plurality of chromatically selective scattering particles having a particle size distribution as measured by (weight average diameter)/(number average diameter) of less than or equal to about 1.1, and a colorant; and the at least one indicia exhibits a change in color in response to the environmental stimulus.

18 Claims, 3 Drawing Sheets

PRINTED INDICATOR COMPOSITIONS

FIELD

The invention generally relates to the use of scattering particles in coatings and printing inks and in particular to methods of revealing the environmental exposure of substrates containing these coatings and printing inks.

SUMMARY

In one aspect, a method of revealing exposure of a substrate to an environmental stimulus is provided including exposing the substrate to the environmental stimulus. In some embodiments, the substrate includes at least one indicia, where each of the at least one indicia includes a plurality of chromatically selective scattering particles (CSSPs) having a particle size distribution as measured by (weight average diameter)/(number average diameter) [i.e. Dw/Dn] of less than or equal to about 1.1, and a colorant; and the at least one indicia exhibits a change in color in response to the environmental stimulus. The environmental stimulus may be heat, pressure, liquid or vapor. In some embodiments, the method may further include observing the change in color of the at least one indicia. In some embodiments, the at least one indicia is at least a first indicia and a second indicia; and the CSSPs in the first indicia have a glass transition temperature that is different from a glass transition temperature of the CSSPs in the second indicia. In some embodiments, the first indicia changes color in response to the environmental stimulus and the second indicia does not change color, or alternatively, both first and second indicia change color in response to the environmental stimulus. In certain embodiments both first and second indicia change color in response to the environmental stimulus but the amount of color change in the first indicia is different from the amount of color change in the second indicia. In certain other embodiments both first and second indicia do not change color in response to a stimulus indicating that the applied stimulus was not sufficient or was below a threshold needed to cause a color change.

In some embodiments, the CSSPs include polymeric particles. In some embodiments, the CSSPs include cross-linked polymeric particles. In some embodiments, the polymeric particles have a glass transition temperature from about 20° C. to about 180° C. In some embodiments, the polymeric particles have a glass transition temperature from about 40° C. to about 140° C.

In another aspect, a method for authenticating the identity of a consumer goods package is provided, including applying a first identifying indicia to a consumer goods package; overlaying at least a portion of the first identifying indicia with a first concealing indicia to conceal the portion of the first identifying indicia; where the first concealing indicia comprises a plurality of CSSPs having a particle size distribution as measured by (weight average diameter)/(number average diameter) of less than or equal to about 1.1; and a colorant; and applying an identity revealing stimulus to the first concealing indicia to reveal a portion of the first identifying indicia. In some embodiments, a color of the first concealing indicia matches a color of the first identifying indicia. In some embodiments, the method further comprises examining the revealed first identifying indicia to authenticate the identity of the package.

In other embodiments, the method further includes applying one or more additional identifying indicia on the consumer goods package and overlaying the one or more additional identifying indicia with one or more additional concealing indicia, where each of the one or more additional concealing indicia comprises a plurality of CSSPs having a particle size distribution as measured by (weight average diameter)/(number average diameter) of less than or equal to about 1.1; and a colorant. In some embodiments, the method further includes applying a protective layer over the first concealing indicia.

In some embodiments, the CSSPs comprise an emulsion polymer. In other embodiments, a weight average diameter of the CSSPs is from about 125 to about 700 nm. In embodiments where one or more additional concealing indicia are used, the weight average diameter of the CSSPs of each of the one or more additional concealing indicia and a weight average diameter of the CSSPs of the first concealing indicia are substantially different. As used in this context, "substantially different" means that the weight average diameter of the CSSPs in the regions being compared are dissimilar enough that each can impart different properties to the concealing indicia. For example, the weight average diameter of the CSSPs in one region that is substantially different from those in another region will have detectable difference in color, response to external stimuli, or the like. Additionally different colorants may be used with CSSPs of different particle sizes so that they are different in color and in their response to the external stimulus.

In another aspect, a temperature sensor is provided including a substrate; and a first region of concealing indicia overlaying and concealing a first region of a temperature identifying indicia applied to the substrate; where the first region of concealing indicia includes a plurality of CSSPs having a particle size distribution as measured by Dw/Dn of less than or equal to about 1.1 and a glass transition temperature, and a colorant. In some embodiments, when the concealing indicia is exposed to an external temperature exceeding the glass transition temperature, at least a portion of the plurality of CSSPs undergo deformation in the first region of the concealing indicia to reveal the first region of the temperature identifying indicia.

In another aspect, an identification system is provided including a substrate; and a first region of concealing indicia each overlaying and concealing a first region of an identification indicia applied to the substrate; where the first region of concealing indicia includes a plurality of CSSPs having a particle size distribution as measured by Dw/Dn of less than or equal to about 1.1, and a colorant; and when the first region of concealing indicia is exposed to a first external stimulus at least a portion of the plurality of CSSPs undergo deformation to reveal the first region of the identification indicia.

In another aspect, an identification system is provided including a substrate; and a plurality of concealing indicia regions, each overlaying and concealing a corresponding region of an identification indicia applied to the substrate; where each of the plurality of concealing indicia regions independently includes a plurality of CSSPs having a particle size distribution as measured by Dw/Dn of less than or equal to about 1.1, and a colorant; the plurality of CSSPs in each of the plurality of concealing indicia regions has a different weight average diameter; and when the substrate is exposed to an external stimulus a portion of each of the plurality of concealing indicia regions independently undergo deformation or does not deform, to reveal or remain concealing, the corresponding region of identification indicia.

In another aspect, a temperature sensor is provided including a substrate; and a region of temperature identifying indicia applied to the substrate; where the temperature identifying indicia includes a plurality of CSSPs having a particle size distribution as measured by Dw/Dn of less than or equal to about 1.1, and a glass transition temperature, and a colorant. In some embodiments, when the temperature identifying indicia is exposed to an external temperature exceeding the glass transition temperature, at least a portion of the plurality of CSSPs undergo deformation to cause change in color of the temperature identifying indicia.

In another aspect, an identification system is provided including a substrate; and a region of an identification indicia applied to the substrate; where the identification indicia includes a plurality of CSSPs having a particle size distribution as measured by Dw/Dn of less than or equal to about 1.1, and a colorant; and when the identification indicia is exposed to a first external stimulus at least a portion of the plurality of CSSPs undergo deformation to cause change in color of the of the identification indicia.

In another aspect, an identification system is provided including a substrate; and a plurality of indicia regions, where each of the plurality of indicia regions independently includes a plurality of CSSPs having a particle size distribution as measured by Dw/Dn of less than or equal to about 1.1, and a colorant; the plurality of CSSPs in each of the plurality of indicia regions has a different weight average diameter; and when the substrate is exposed to an external stimulus a portion of each of the plurality of indicia regions independently deform or does not deform, to cause change in color or no change in color in, the corresponding region of identification indicia.

In another aspect, a method for authenticating the identity of a consumer goods package is provided including applying an identity revealing stimulus to a consumer goods package to reveal at least one identifying indicia, and examining the at least one identifying indicia to authenticate the consumer goods package; where the consumer goods package includes the at least one identifying indicia including a plurality of chromatically selective scattering particles having a particle size distribution as measured by Dw/Dn of less than or equal to about 1.1; and a colorant.

DETAILED DESCRIPTION

Chromatically selective scattering particles (CSSPs) may be incorporated into coatings for use in packaging. The coatings may be used to reveal information regarding the package. For example, information regarding the authenticity, or the shipment environment of the package may be encoded in the coating and revealed. According to some embodiments, such methods may be used in reducing, or identifying counterfeiting of products, authenticating goods vs. grey or black market goods, and the like. For example, the reproduction of a combination of a multitude of indicia with different colors and different but defined degrees of color shifting and with defined switching temperatures is very difficult as it needs in-depth understanding of the process and high accuracy to produce it, like a hologram image, a watermark or other complex pattern. In addition, the consumer goods packaging may contain a concealed logo or message that is not readily apparent to a counterfeiter, but, if not present, would indicate that the goods contained in the packaging are not authentic.

According to other embodiments, such methods may be used to track the thermal history of a package or other substrates having the coatings. Thermal history of packages is important in determination of the usefulness of package contents in many cases. For example, exposure of certain types of foods to temperatures above or below a threshold value may cause deterioration so that the food is no longer suitable for consumption. Many types of drugs can also undergo changes making these unsuitable for use when exposed to temperature above a threshold value. In other examples such as in pasteurization of foods thermal history of the sample provides an indication when the food is ready for consumption. In certain other cases, thermal history of a sample may indicate whether the food contained is overheated leading to undesirable change in taste.

Figure 1:
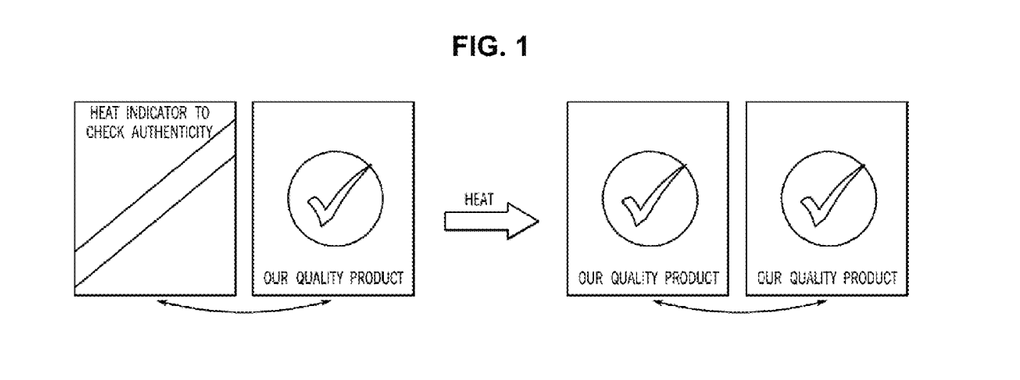
FIG. 1 is an illustration of an authentication indicia before and after treatment with heat, according to one embodiment.

In one aspect, the coatings include at least one indicia printed or coated on a substrate, such as a package. The at least one indicia may be a picture, text, a logo, a bar code, or other pattern. The indicia includes a plurality of CSSPs having a particle size distribution as measured by Dw/Dn of less than or equal to about 1.1. When exposed to an environmental stimulus such as heat, pressure, and/or solvent, the indicia changes color due to a change in the light scattering of the CSSPs, thereby revealing information that may be encoded in the picture, text, logo, bar code, or other pattern. FIG. 1 is one such example. Such color changes may be detectable visually, or using instrumentation known to those of skill in the art, such as a spectrophotometer or densitometer. Some compositions comprising CSSPs disclosed herein are useful in revealing color change with as little as 0.5 $\Delta E^*$(CIE Lab) identifiable by the human eye. It is believed that the color change is caused by deformation of the CSSPs in response to the environmental stimulus. In certain embodiments the deformation of CSSPs may be accompanied by flow leading to coalescence of the polymeric particles.

In another aspect, the coatings may be two-part coatings, where a first part, an identification indicia, is applied to a substrate, and then a second part, a concealing indicia incorporating CSSPs, overlays the first part. When a stimulus is applied to a substrate having the indicia, the light scattering of the CSSPs change to reveal the identification indicia. The coatings (i.e. identification or concealing indicia) may be inks or other marking coatings which are printed or coated onto a substrate such that information may be conveyed to an observer. Such information may be a color, a logo such as a design or picture, a word, a bar code, a number, or any such mark. The concealing indicia may be a coating such as an ink or a paint which effectively conceals the underlying identifying mark. The concealing indicia may be opaque, such that the underlying mark is obliterated by the overlying indicia. Alternatively, the concealing indicia may be somewhat transparent, mimicking the color of the underlying identifying mark, such that the underlying mark is effectively screened from observation. The CSSPs are well-suited to either application. CSSPs may be used to tune an indicia to a specific color, thus they are suited to color-matching or color-mimicking.

As used herein, "scattering particles" are considered to be "chromatically selective" if they preferentially scatter a portion of the visible light such that they modify the incident spectral power distribution. In other words, the CSSPs, when added to a coating, will make the coating appear to be of a color that is altered as compared to the coating without the CSSPs. For example, CSSPs added to black coating, can make the perceived color of the otherwise black coating appear to be any of a range of colors including blues, greens, reds, yellows, or a combination thereof. The exact color depends upon the particle sizes of the particles of the CSSPs. When CSSPs are added to coatings of a color other than black, they can also make the perceived color of the coating appear to shift or be enhanced. For example, if CSSPs that scatter light to appear blue are added to a blue coating, the blue coating appears "bluer" and brighter than the blue coating without the CSSPs. Similarly, if CSSPs that scatter light to appear red are added to a blue coating, color mixing can occur to make the perceived color appear purple (i.e. the product of mixing of the blue pigment with the CSSPs that scatter to perceive red). Other colored pigments may be enhanced, and other color mixing can be achieved depending upon the pigment selected and the size of the CSSP selected.

Without wishing or intending to be bound to any particular theory of the invention, it is believed that the CSSPs can be used to change the perceived color of material due, at least in part, to the void volume between the CSSPs. For example, nearly monodisperse particles of the CSSPs may form a close-packed array with a void volume in the dried film of approximately 26%. In some embodiments, the close-packed array is a nearly crystalline array. The void volume is filled with air or another suitable medium to provide a surrounding medium having a refractive index that is sufficiently different from the refractive index of the CSSPs to produce noticeable light scattering at the interface between the voids and the CSSPs. The CSSPs may be made from a variety of materials, including both organic and inorganic materials.

In some embodiments the CSSPs are polymeric particles. Such particles include, but are limited to, particles polymerized from vinyl aromatic monomers, (meth)acrylic acid and/or various derivatives of (meth)acrylate monomers. Suitable monomers include, but are not limited to styrene, α-methylstyrene, butadiene, vinyl acetate, (meth)acrylic acid, 2-hydroxyethyl acrylate, methyl methacrylate, butyl acrylate and 2-ethylhexyl acrylate. In certain embodiments of this invention, polymeric CSSPs with narrow particle size distribution (PSD) are made by emulsion polymerization. Emulsion polymerization is a well known technique based on free radical initiated polymerization of monomers in an aqueous medium in the presence of surface active agents. A variety of monomers can be used for the preparation of emulsion particles. A number of techniques for generation of free radical initiators are also known. Emulsion polymers with narrow PSD and specific Dw can be made by the appropriate selection of process variables. These emulsion polymers can be made by a seeded or unseeded process. Further, a batch, semi-continuous or continuous process can be used. Emulsion polymers may also be cross-linked in order to improve their resistance properties. The selection of monomers for emulsion polymers is made on the basis of refractive index, glass transition temperature ($T_g$), polarity and other properties. These principles are known to persons of ordinary skill in the art. For example, the glass transition temperature (Tg) of a polymer can be calculated from the glass transition temperature of its component monomers by use of the following equation.

$$1/T_g = \Sigma(w_i/T_{gi})$$

where $w_i$ is weight fraction of monomer and $T_{gi}$ is glass transition temperature of the homopolymer of this monomer. The values of $T_g$ for homopolymers can be found in the *Polymer Handbook, Third edition*, Brandrup and Immergut, editors, John Wiley and Sons, New York, 1989, Ch VI, pp. 213-258. Therefore, a person skilled in the art can use the above equation in order to formulate a polymer with specific $T_g$. In addition, Tg may be adjusted downward through the use of materials commonly known as plasticizers. Also crosslinking of certain polymer particles with metals can be used to increase Tg of polymeric particles.

It is known that the refractive index of a polymer is an additive function of the refractive indices of homopolymers of monomers contained in the polymer. The following equation can be used to calculate the refractive index of a polymer.

$$n = \Sigma(v_i n_i)$$

In this equation, $n_i$ is the refractive index and $v_i$ is the volume fraction of the monomer present in the polymer. Values of refractive indices for a variety of polymers are given in the *Polymer Handbook, Third Edition*, Brandrup and Immergut, editors, John Wiley and Sons, New York, 1989, Ch VI, pp. 451-461.

Cross-linked emulsion polymers may be made in a variety of ways using methods known to persons of ordinary skills in the art. In certain embodiments, cross-linked emulsion polymers can be prepared by copolymerization of polyolefinically unsaturated monomers with other monomers described above. Examples of polyolefinically unsaturated monomers and diacrylates and dimethacrylates of alkanediols of about 1 to 8 carbon atoms, such as glycol diacrylate and dimethacrylate, butane-1,4-diol diacrylate and dimethacrylate, hexane-1,6-diol diacrylate and dimethacrylate, octane-1,8-diol diacrylate and dimethacrylate, as well as divinylbenzene, diallyl phthalate, butadiene and trimethylolpropane triacrylate or trimethacrylate, and pentaerythritol triacrylate or tetraacrylate. The polyolefinically monomers may used in an amount of from 0.05 to 15% by weight, based on the total amount of monomers to be polymerized.

In certain other embodiments, cross-linked emulsion polymers can be prepared by copolymerization of crosslinking monomers with other monomers described above. Examples of crosslinking monomers include epoxy (usually glycidyl) and hydroxyalkyl-methacrylates and -acrylates, as well as keto- or aldehyde-functional monomers such as acrolein, methacrolein and vinyl methyl ketone, the acetoacetoxy esters of hydroxyalkyl (usually $C_1$-$C_{12}$)acrylates and methacrylates such as acetoacetoxyethyl methacrylate and acrylate, and also keto-containing amides such as diacetone acrylamide. In some embodiments, the hydroxyalkylmethacrylates are hydroxy($C_1$-$C_{12}$-alkyl)methacrylates. For example, hydroxyethylmethacrylate is the $C_2$-alkyl member of the series. In some embodiments, the hydroxyalkylacrylates are hydroxy($C_1$-$C_{12}$-alkyl)acrylates. For example, hydroxyethylacrylate is the $C_2$-alkyl member of the series.

In other embodiments, the CSSPs are inorganic particles. Such particles include, but are not limited to, silica particles, glass particles and titanium dioxide particles.

The CSSPs may be solid particles, hollow particles or a combination thereof. Suitable hollow particles include microspheres with voids. Examples of suitable microspheres include polymeric, glass and ceramic microspheres. The polymeric microspheres may be made from a variety of polymers, however, preferred microspheres are composed of styrene-acrylic copolymers. The dimensions of the void provided by the microspheres are desirably between 170 and 360 nm and the size distribution (i.e., Dw/Dn) of the void is desirably no more than 1.1. In some embodiments, the dimensions of the void provided by the microspheres are desirably between 170 and 360 nm and the Dw/Dn of the void is desirably no more than 1.1. Suitable microspheres for use in the present color enhancing compositions include those described in U.S. Pat. No. 4,089,800, the entire disclosure of which is incorporated herein by reference.

In some embodiments, a combination of hollow sphere CSSPs and non-hollow sphere CSSPs of similar composition may be used. Upon application of a solvent medium having a refractive index that matches or nearly matches the refractive index of the CSSPs (e.g., a solvent selected such that the ratio of refractive indices of the CSSPs and medium is no more than about 1.1), the voids contained within the hollow sphere CSSPs remain while the voids between the spheres are filled with the medium. As a result the scattering characteristics, and therefore the color, of the regions containing the hollow sphere CSSPs remain unchanged or substantially unchanged, while the scattering characteristics, and therefore the color, of the regions containing non-hollow sphere CSSPs change. Removal or drying of the solvent can result in a reversible change.

In some embodiments, the CSSPs have a particle size distribution (i.e., Dw/Dn) of no more than about 1.1. This includes embodiments where the CSSPs have a particle size distribution of no more than about 1.01. This further includes embodiments where the CSSPs have a particle size distribution of no more than about 1.001. In some embodiments, the CSSPs have a weight average diameter (Dw) from about 125 to about 700 nm. In some embodiments, the CSSPs have a weight average diameter (Dw) from about 125 to about 150 nm. In some embodiments, the CSSPs have a weight average diameter (Dw) from about 150 to about 175 nm. In some embodiments, the CSSPs have a weight average diameter (Dw) from about 175 to about 200 nm. In some embodiments, the CSSPs have a weight average diameter (Dw) from about 200 to about 225 nm. In some embodiments, the CSSPs have a weight average diameter (Dw) from about 225 to about 250 nm; from about 250 to about 275 nm. In some embodiments, the CSSPs have a weight average diameter (Dw) from about 275 to about 300 nm. In some embodiments, the CSSPs have a weight average diameter (Dw) from about 300 to about 325 nm. In some embodiments, the CSSPs have a weight average diameter (Dw) from about 325 to about 350 nm. In some embodiments, the CSSPs have a weight average diameter (Dw) from about 350 to about 375 nm; from about 375 to about 400 nm. In some embodiments, the CSSPs have a weight average diameter (Dw) from about 400 to about 425 nm. In some embodiments, the CSSPs have a weight average diameter (Dw) from about 425 to about 450 nm. In some embodiments, the CSSPs have a weight average diameter (Dw) from about 450 to about 475 nm. In some embodiments, the CSSPs have a weight average diameter (Dw) from about 475 to about 500 nm. In some embodiments, the CSSPs have a weight average diameter (Dw) from about 500 to about 525 nm. In some embodiments, the CSSPs have a weight average diameter (Dw) from about 525 to about 550 nm. In some embodiments, the CSSPs have a weight average diameter (Dw) from about 550 to about 575 nm. In some embodiments, the CSSPs have a weight average diameter (Dw) from about 575 to about 600 nm. In some embodiments, the CSSPs have a weight average diameter (Dw) from about 600 to about 625 nm. In some embodiments, the CSSPs have a weight average diameter (Dw) from about 625 to about 650 nm. In some embodiments, the CSSPs have a weight average diameter (Dw) from about 650 to about 700 nm. These ranges are merely exemplary and are not discreet in and of themselves. Any range within the broader about 125 nm to about 700 nm range may be indicated where the particles conform to the other particle size distribution requirements. As used herein, the term "diameter" refers the length of the largest internal diameter of a particle. Concomitantly, because the color of light that is scattered by the CSSPs is specific to the size of the CSSPs, measuring the color of an indicia will provide information regarding the particle size of the CSSPs in that indicia.

Color alteration due to light scattering from the CSSPs is due, in part, to the relationship between particle size and the reflectance spectrum of the colorant. Thus, in some embodiments, a ratio of the weight average diameter of the CSSPs to a wavelength maximum in the transmission or reflectance spectrum of the colorant is between about 0.3 and 0.6, or between about 0.4 and 0.5, in other embodiments.

Where the CSSPs are formed of a polymeric material, the CSSPs have an associated glass transition temperature. Where the glass transition temperature is exceeded, the CSSPs change their particle shape, which in turn effects the light scattering of the CSSPs in the indicia and a color change is manifested. Hence, in some embodiments, the CSSPs have a glass transition temperature of from about 0° C. to about 150° C. In other embodiments, the CSSPs have a glass transition temperature of from about 20° C. to about 120° C. In other embodiments, the CSSPs have a glass transition temperature of from about 20° C. to about 180° C. In other embodiments, the CSSPs have a glass transition temperature of from about 40° C. to about 140° C. CSSPs having a narrow particle size distribution and a well defined glass transition temperature may be able to encode temperature related information that is accurate to about ±10° C., about ±5° C., about ±4° C., about ±3° C., about ±2° C., or about ±1° C., in various embodiments.

In some embodiments, the application of heat to polymeric CSSPs surpasses the glass transition temperature and the polymers may then undergo deformation. As used herein, the term "deformation" indicates that the CSSPs move within the bulk indicia to coalesce and thereby change the scattering properties of the indicia.

The CSSPs incorporated in the indicia typically have a surrounding medium which is simply a medium that occupies the volume between the particles. There should be sufficient refractive contrast between the CSSPs and the surrounding medium to provide chromatically selective scattering. Typically, it is sufficient that the ratio of the refractive indices (RI) of the two phases is at least about 1.2. In some embodiments, the surrounding medium may be a polymer, including a resin or a binder. In other embodiments, the surrounding medium is air contained in voids that are present between the particles when the compositions are dried into a film. In still other embodiments, the surrounding medium may actually be defined by empty voids (i.e., a vacuum) between the particles. In still other embodiments the surrounding medium may be composed of both a binder, such as a polymer or resin, and air-filled voids or vacuum. The surrounding medium may be a water-based, or solvent-based medium. Such binders (i.e., mediums) well known in the art. When the surrounding medium is air or a vacuum the particles should not completely coalesce during or after the application and drying of the composition on a substrate, so that the air-filled voids or vacuum remain present when the composition is dried into a film.

Suitable substrates for use with the indicia having CSSPs include most known substrates or surfaces. Exemplary substrates include, but are not limited to, paper and paperboard, glass, metal, plastic and rubber substrates. The identifying and concealing indicia may be applied by any means known to those of skill in the art. For example and without limitation, the indicia may be applied by coating, such as with a blade, a draw knife, an air-knife, a paint brush, spin coating, curtain coating or via printing such as by laser jet, ink jet, flexographic, gravure, rotogravure, lithography or screen printing. As with many types of packaging, the indicia may be overcoated with a protective layer. Suitable protective layers include, but are not limited to, a transparent or semi-transparent coatings or laminations such as a plastic. In some embodiments, the indicia may be applied to a portion of the substrate which may then be adhered to the consumer package using suitable means such as a glue, adhesive or a pressure sensitive adhesive.

In some embodiments, the colorant that is present in the indicia is a pigment or a dye. A wide range of pigments and dyes known to those of skill in the art may be used, including blacks, blues, reds, greens, yellows, and mixtures thereof. A brief listing of some exemplary pigments and dyes may include carbon black, phthalocyanine blue, perylene black, azo dyes including metalized azo dyes, carbocyclic azo dyes and heterocyclic azo dyes, polymethine dyes, quinophthalones, sulfur dyes, nitro and nitroso dyes, cyanines, diazacarbocyanine, anthraquinone, other pigments, etc.

Where the indicia includes CSSPs, the CSSPs may be loaded to various levels. In some embodiments, indicia includes CSSPs at a level of about 50 to about 99.9 weight percent of the dried coating or ink, or from about 60 to about 99 weight percent of the dried coating or ink. Such indicia may be in the form of an ink, a paint, or other coating as is known in the art. The solvent is allowed to evaporate after application in order to obtain the dried ink, paint or coating. The color development becomes most visible in the dry state.

The amount of indicia that is deposited in a coating may vary across a wide spectrum, based upon the needs of the end user, or the application process. However, in general the thickness of the dried coating may range from about 0.5 µm to about 10 µm, from about 1 µm to about 5 µm, or from about 2 µm to about 5 µm, according to various embodiments.

As noted above, in one aspect, the coatings include at least one indicia printed or coated on a substrate, such as a package, and the at least one indicia may be the whole of, or part of, a picture, text, a logo, a bar code, or other pattern. The indicia includes a plurality of CSSPs having a particle size distribution as measured by $D_w/D_n$ of less than or equal to about 1.1. When exposed to an environmental stimulus such as heat, pressure, and/or solvent, the indicia changes color due to a change in the light scattering ability of the CSSPs, thereby revealing information that may be encoded in the picture, text, logo, bar code, or other pattern. In other embodiment the color change of different indicia makes a certain picture, text, logo, bar code, or other pattern switch into another defined but different picture, text, logo, bar code, or other pattern.

Indicia may also be susceptible to varying degrees of the same stimuli. For example, two, or more different regions of indicia may individually have CSSPs that respond to a particular stimulus, i.e. temperature, pressure, or solvent, but the different regions exhibit color changes at different temperatures, different pressures, or with different solvents. Thus, two, or more different temperatures, pressures, or solvents may be required for full authentication of the package.

In one embodiment, the indicia is coated on a package substrate as an indicator of the authenticity or branding of an item against counterfeiting. Such indicia include information that may be known to a brand manufacturer, but would otherwise be unknown to a counterfeiter. For example, a brand manufacturer applies a bar code, and for reasons of simplicity in this example, the bar code has two bars: a left bar and a right bar. Upon application of heat or pressure of a given magnitude, or a solvent or combination of solvents, to both bars, one or both of the bars may undergo a change in color. However, when a counterfeiter prints the indicia, and attempts to copy the colors and other identifying parts of the mark, it will not be known which, or if, a bar changes color, thereby making duplication difficult. Furthermore, given complex bar codes or other patterns, complex branding identification patterns may be incorporated, or they may change at random or predetermined intervals, thereby adding further complexity to attempted counterfeiting. In one embodiment, a visually similar pattern may be printed next to a switchable pattern based on CSSPs. Upon application of stimulus the switchable pattern will change to match the non-switchable pattern thus providing a means for ready confirmation of the authenticity.

Figure 2:
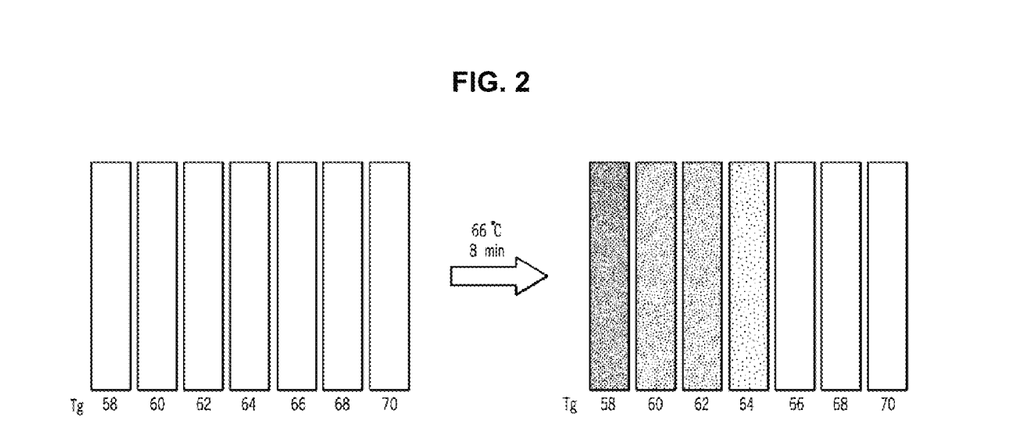
FIG. 2 is a non-limiting illustration of a temperature sensor with a set of multiple indicia areas with slightly varying MFT/Tg. Multiple indicia areas may be used to increase the accuracy of the temperature sensor.

According to another embodiment, the indicia may be used as a temperature sensor. The temperature sensors may be used in packaging or displays where a historical record, i.e. thermal history, of the packing or display is desired. The temperature reading of the sensor may be printed or coated on a substrate as an indicia in the form of a thermometer, text, a bar code, or other pattern or symbol. When a particular temperature is exceeded the indicia changes color to reveal either the fact that the particular temperature was exceeded, or that the particular temperature was attained. For example, a single indicia may change color when a particular temperature, known to an observer, is exceeded. Alternatively, temperatures may be expressed in the indicia as a numerical value or in the form of a code that will appear to be of a specific pattern at a variety of temperatures, such that an observer can determine the temperature to which the indicia was exposed. CSSPs having well defined glass transition temperatures may be used in temperature indicating indicia to determine a temperature to within 5° C. in some embodiments, to within 4° C. in some embodiments, to within 3° C. in some embodiments, to within 2° C. in some embodiments, to within 1° C. in some embodiments, or in yet other embodiments, to within less than 1° C. A set of multiple indicia areas with slightly varying Tg will make the temperature sensor even more accurate (FIG. 2).

The temperature at which polymeric CSSPs respond in a temperature sensor is related to the chemical properties of the polymeric material, which contribute to the observed glass transition temperature for the CSSPs. For example, a particular polymer will have an associated glass transition temperature ($T_g$), however the speed in which the polymer exhibits an observable change will depend upon the size of an item made with the polymer. Also, a narrow particle size distribution (PSD) will allow for a more uniform observable change and a deeper color impression as opposed to a more diffuse PSD.

The manner in which such temperature sensors may be used is limited only by the imagination of the user. Items such as food stuffs or pharmaceuticals can be deleteriously affected by exposure to heat during shipping. The following examples are provided merely for explanation and are not in any way limiting. For example, some antibiotics are temperature sensitive and cooler temperatures are required during shipment to avoid the deleterious effects of higher temperatures on the materials. Other pharmaceuticals are also known to be adversely affected by exposure to elevated temperatures. Other examples include wine shipments, or other food shipments, where flavor profiles are altered by exposure to a given temperature. Pasteurized and non-pasteurized foods may be adversely affected by exposure to elevated temperatures. For example, pasteurization requires that the material to be pasteurized be heated at a temperature of 66° C. for a given time. The present indicators can aid in the determination that the pasteurization was complete. Novelty items may also incorporate such temperature sensors. Such temperature sensors, or indicators, on the shipment packaging or product packing, may be used to ensure product integrity.

Temperature sensors may be incorporated in the packaging for the bulk materials, or even the individual containers, to convey to a recipient that the contents were exposed to a temperature of a given magnitude. Alternatively, messages such as "Do Not Use," or "Thermally Exposed" or "food is medium/well-done, etc" may be used as the temperature sensor to provide a warning that the contents may no longer be suitable for their intended use. Alternatively, a color change may be apparent to indicate that a given temperature was exceeded. For example, the color change may correspond to a color key, or the color change may be via comparison of the temperature sensor to a block of the same color that is not affected by temperature exposure.

In addition to providing a temperature indication, the length of time that a substrate was exposed to the temperature may also be determined. Because a color change in an indicia incorporating CSSPs is tied to both temperature to which a substrate having the indicia is exposed, and the length of time of the exposure, the degree of color change may be used to gauge how long a given temperature was applied. In some embodiments, exposures of from minutes to hours to weeks of exposure may be readily detectable, and can be calibrated to standards to determine the time of exposure to within specific limits. In other embodiments pasteurization and/or sterilization can be monitored. The exact time temperature profile of CSSPs may require to be calibrated for each application.

In certain embodiments, an identification indicia which does not incorporate CSSPs, is applied to a region of the substrate, and then another indicia incorporating CSSPs, is applied to at least same region of the substrate so that the identification indicia is not visible. To reveal the identifying indicia, an external stimulus may be applied. The external, or environmental, stimulus may cause a change in the scattering properties of the CSSPs thereby revealing the underlying identification mark. In some embodiments, the identifying indicia changes color to effect the revealing of the underlying indicia. In other embodiments, the methods also include observing the identification indicia. Once the identification indicia has been observed, authentication of the consumer goods package may occur.

Methods may further include applying one or more additional identifying indicia to the consumer goods package. Different regions of identifying indicia that are susceptible to different external stimuli may be used. This may allow for revealing the identity or authenticity of the consumer goods package by a variety of stimuli or in different environments. For example, the CSSPs in one of the regions may have a change in their scattering properties in the presence of heat of a specific temperature range, and other regions may change their scattering properties by the application of pressure or solvent. Therefore, at least two types of external stimuli may be needed to reveal enough of the identifying indicia needed to authenticate the consumer goods package or increase the degree of complexity needed for a counterfeit marker.

According to one embodiment, the identifying indicia containing CSSPs may also be incorporated into a temperature sensor. The temperature sensors may be used in packaging or displays where a historical record of the packing or display is desired. The temperature reading of the sensor may be printed or coated on a substrate as an indicia. The temperature dependent properties of the coating are imparted by the incorporation of CSSPs into the coating.

Where the temperature indicating indicia is a temperature scale, multiple regions of identifying indicia may be used to reveal a temperature on the scale that corresponds to the individual temperature. Each of the multiple regions individually have an associated temperature at which the CSSPs in that region will deform. When a substrate having a temperature scale identified by multiple indicia regions is exposed to an applied temperature, all identifying indicia regions in which the associated CSSPs deform at a temperature that is less than the applied temperature will deform and reveal the underlying temperature indication.

Two-part coatings may also be incorporated into identification, or authentication systems. The identification system may be used in packaging or displays. The identification system may use one or more regions of identification indicia that are concealed by one or more regions of concealing indicia. Each region of concealing indicia includes a plurality of CSSPs of a narrow particle size distribution and a colorant.

The identification indicia may be printed or coated onto a substrate. The identification indicia may be a symbol, one or more words, a bar code, a colored indicia, or a combination of any two or more thereof. The identifying indicia will convey to an observer, some meaning or identification. For example, the substrate may be a packaging or display that requires an identifying mark. It may be desirable to conceal that mark until a time as it's display is required or is triggered by a certain event. At such a point, a first external stimulus may be applied that causes at least a portion of the CSSPs in the identifying indicia to deform and reveal the underlying identifying indicia.

In one embodiment, the identifying indicia is of a color that is of same color as that of its surrounding region. Upon application of the external stimulus, the CSSPs in the identifying indicia reveal the underlying indicia due to a change in color so that the indicia is of a different color than the surrounding region. In other embodiments, identifying indicia is of a color that is different than that of its surrounding region. Upon application of the external stimulus the CSSPs in the identifying indicia change the apparent color of the identifying indicia to match the color of the surrounding media, thereby camouflaging it from observation.

A plurality of regions of identification indicia may be applied to a substrate and each region of identification indicia may respond differently to different external stimuli. For example, if the stimulus is heat and a first temperature is applied, only one of the identification indicia CSSPs may deform to reveal the indicia. The application of a second, higher temperature, may then be used to cause the CSSPs in other regions to deform. A plurality of such systems may be used. Similarly, regions may be individually prepared to react to different temperatures, different solvent, or different pressures, or a combination of any of these.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present embodiments, thus generally described, will be understood more readily by reference to the following examples, which are provided by way of illustration and are not intended to be limiting of the present technology in any way.

EXAMPLES

Abbreviations:
The following abbreviations are used throughout:
APS is ammonium persulfate;

CSSP is chromatically selective scattering particle
DI water is de-ionized water;
$D_n$ is the number average diameter;
$D_w$ is the weight average diameter:
EHA is 2-ethylhexyl acrylate;
HEA is 2-hydroxyethyl acrylate;
MAA is methacrylic acid;
ST is styrene; and
$T_g$ is glass transition temperature.

Measurements and Equipment:

The viscosity of emulsions was measured by a Brookfield Model DV-II+ viscometer. The spindle size and RPM used for these measurements is given. Particle size of emulsions was measured with a Capillary Hydrodynamic Fractionation (CHDF) model 2000 from Matec Instruments. The values of $D_n$ and $D_w$ are reported. The non-volatile content of emulsions was measured from the weight loss of an approximately 1 g size sample heated in an oven at 145° C. for 30 minutes. pH was measured with a pH meter.

Unless otherwise specified, amounts listed in the tables that follow are in grams (g).

Example 1

A Seed Latex. In a vessel, a monomer mixture was prepared by blending MAA (23.9 g), HEA (26.4 g), EHA (83.8 g), ST (703.5 g), a 75% by weight solution of sodium dioctyl sulfosuccinate in water (Aerosol OT-75) (10.9 g), and DI water (249.9 g).

An aliquot of the monomer mixture (219.7 g) was then added to a separate, heated, 3 liter reactor, containing DI water (783 g) at 75° C. APS (3.0 g) was separately dissolved in DI water (12.0 g) and added to the reactor, followed by additional DI water (28.3 g) and the mixture stirred.

The reactor temperature was maintained just below 80° C. After 20 minutes of stirring, the remaining monomer mixture prepared above was fed to the reactor at a constant rate over 100 minutes. After the monomer feed was completed, the reaction was held for 60 min, after which the reaction was cooled, and DI water (75 g) added to form an emulsion.

The resulting emulsion had a non-volatile content of 42% and a pH of 2.0. The particle size of the emulsified polymer was measured on a CHDF instrument, and was determined to have a Dn=116 nm, and a Dw=120 nm.

Examples 2-5

Red and Blue mono-disperse styrene-acrylic emulsion lattices made with seed latexes of varying $T_g$. CSSPs were made using a seeded process for product identification applications. The formulas are shown in Table 1.

TABLE 1

Formulas for Examples 2-5

| Item | Component/Condition | Example 2 | Example 3 | Example 4 | Example 5 |
|---|---|---|---|---|---|
| A | DI water | 108.9 | 108.9 | 108.9 | 108.9 |
|   | Temperature | 78° C. | 78° C. | 78° C. | 78° C. |
| B | MAA | 12.0 | 12.0 | 12.0 | 12.0 |
|   | HEA | 13.3 | 13.3 | 13.3 | 13.3 |
|   | DI water | 120.9 | 120.9 | 120.9 | 120.9 |
|   | Aerosol OT-75 | 6.6 | 6.6 | 6.6 | 6.6 |
|   | ST | 316.2 | 383.6 | 316.2 | 383.6 |
|   | HEA | 80.1 | 12.6 | 80.1 | 12.6 |
| C | Seed from Ex. 1 | 90 | 90 | 60.9 | 60.9 |
| D | APS | 2.0 | 2.0 | 2.0 | 2.0 |
|   | DI water | 39.3 | 39.3 | 39.3 | 39.3 |
|   | Aqueous ammonia, 28% | 0.2 | 0.2 | 0.2 | 0.2 |
|   | Feedtime (min) | 120 | 120 | 120 | 120 |
| E | DI water | 8.3 | 8.3 | 8.3 | 8.3 |
| F | TBHP | 0.78 | 0.78 | 0.78 | 0.78 |
|   | DI water | 1.0 | 1.0 | 1.0 | 1.0 |
| G | Isoascorbic | 1.0 | 1.0 | 1.0 | 1.0 |
|   | DI water | 11.8 | 11.8 | 11.8 | 11.8 |
|   | Aqueous ammonia, 28% | 1.2 | 1.2 | 1.2 | 1.2 |
| H | NaOH 50% | 5.0 | 5.0 | 5.0 | 5.0 |
|   | DI water | 3.1 | 3.1 | 3.1 | 3.1 |
| I | Preserve | 0.3 | 0.3 | 0.3 | 0.3 |
|   | DI water | 2.9 | 2.9 | 2.9 | 2.9 |
| J | DI water | 31.6 | 31.6 | 31.6 | 31.6 |

The following process was used for each of Examples 2-5. Item A of Table 1 was charged to a temperature controlled, agitated 1 L reactor and heated to the specified temperature in Table 1. Mixture B was then separately prepared and approximately 10% of mixture B was added to the reactor, followed by Item C. Mixture D was also separately prepared and added to the reactor. After the additions were completed, the reactor contents were held at the designated temperature for 15 minutes, after which time the remaining mixture B was added over the time specified in Table 1.

Items E and F were then added, and the reaction was held for 5 min. Mixture G was then gradually added over 3-20 minutes. After holding another 5 min., the reaction was cooled to 55° C. or lower. Then mixtures H, I, and J were added in sequence. The physical characteristics of Examples 2-5 are shown in Table 2.

TABLE 2

Physical Characters for Examples 2-5

| Property | Example 2 | Example 3 | Example 4 | Example 5 |
|---|---|---|---|---|
| Non-Volatiles | 55.47 | 54.59 | 55.64 | 55.31 |
| pH | 9.61 | 9.99 | 9.67 | 9.89 |
| Viscosity | 203 | 166 | 173 | 168 |
| Particle size (nm) | 290 | 290 | 322 | 322 |
| $T_g$* (° C.) | 72 | 102 | 73 | 103 |

*Measured at a 15° C./min ramp with differential scanning calorimetry.

Examples 6-9

Ink samples using Examples 2-5 were then prepared. The ink samples were formulated using a carbon black dispersion, and the amounts are presented in Table 3. Draw-downs were done with each of the ink samples using a #12 wire-wound rod. After drying, the ink samples were then tested for color over both white and Kraft paper stock. The samples were also subjected to heat, which impacts the color. The results are reported in Table 4.

TABLE 3

Formulations For Examples 6-9

| Latex | | Wet Weights | |
| --- | --- | --- | --- |
| Example | Example | CSSP (g) | Carbon Black (g) |
| 6 | 2 | 60.0 | 2.0 |
| 7 | 4 | 60.0 | 2.0 |
| 8 | 3 | 60.0 | 2.0 |
| 9 | 5 | 60.0 | 2.0 |

TABLE 4

L*, a*, b* Values For Examples 6-9

| | Color Over White paper stock | | | Color over Kraft paper stock | | |
| --- | --- | --- | --- | --- | --- | --- |
| Example | L* | a* | b* | L* | a* | b* |
| Ambient Temperature | | | | | | |
| 6 | 38.80 | 10.84 | −3.09 | 39.62 | 11.15 | −2.95 |
| 7 | 38.09 | 0.81 | −11.17 | 38.59 | 0.88 | −11.20 |
| 8 | 39.24 | 10.96 | −4.73 | 39.80 | 10.89 | −4.67 |
| 9 | 38.65 | −0.03 | −11.87 | 40.05 | −0.02 | −11.97 |
| 10 Minutes at 80° C. | | | | | | |
| 6 | 22.96 | 0.86 | −3.09 | ND | ND | ND |
| 7 | 38.09 | 0.81 | −11.17 | ND | ND | ND |
| 8 | 39.24 | 10.96 | −4.73 | ND | ND | ND |
| 9 | 38.65 | −0.03 | −11.87 | ND | ND | ND |

ND = not determined.

Color may be characterized by its chromaticity and lightness. The most widely used system of specifying and classifying color was adopted in 1931 by the Commission Internationale de l'Eclairage (CIE), commonly called the International Commission on Illumination. The CIE system revised in 1976, employs a three dimensional "L," "a*" and "b*" chart in which "a*" and "b*" are planar chromaticity coordinates at right angles to one another and "L" is a lightness coordinate at right angle to the plane containing the chromaticity coordinates. In this chart a "+a*" value corresponds to red hue, a "−a*" value at a diametrically opposite end corresponds to green hue, a "+b*" value corresponds to yellow hue and a "−b*" value at a diametrically opposite end corresponds to blue hue. The lightness of color is measured along the "L" axis whereby a higher "L" value corresponds to light of increased intensity and a lower "L" value corresponds to light of decreased intensity. A low or negative "L" corresponds with a grayer, including black, color, while a high or positive "L" corresponds to a brighter, including white, color. Thus, by using this chart any color can be three dimensionally characterized by its chromaticity and lightness. For example, higher "b*" values represent more yellowish hues and lesser bluish hues and lower "b*" values represent more bluish hues and lesser yellowish hues.

In Table 4, the ΔE* values for examples 6-9 on white paper stock after 10 minutes at 80° C. are 19.08, 19.34, 0.10, and 0.02, respectively.

Example 10

Figure 3:
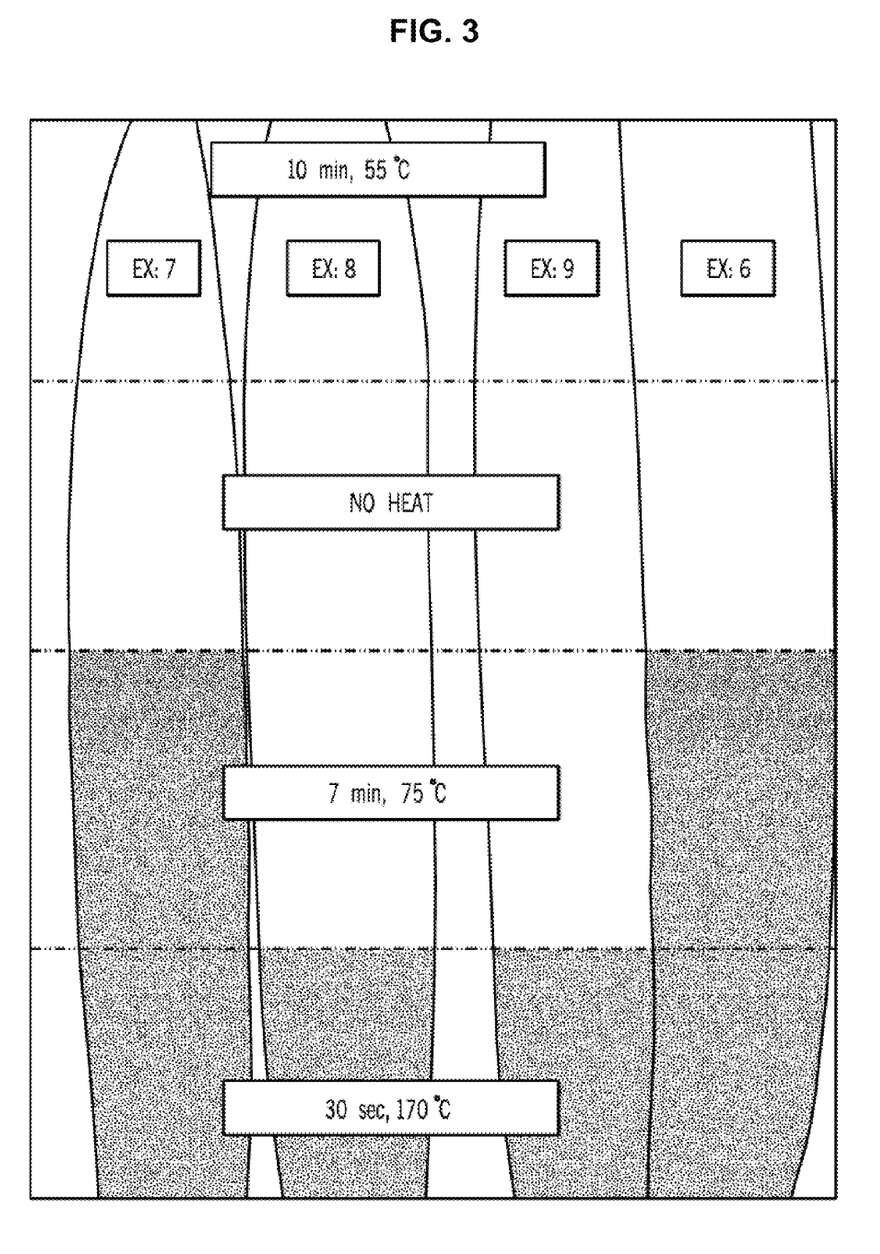
FIG. 3 is a line drawing representation of a photograph of Kraft stock coated with the inks of Examples 6-9 following various heat treatments.
Figure 4:
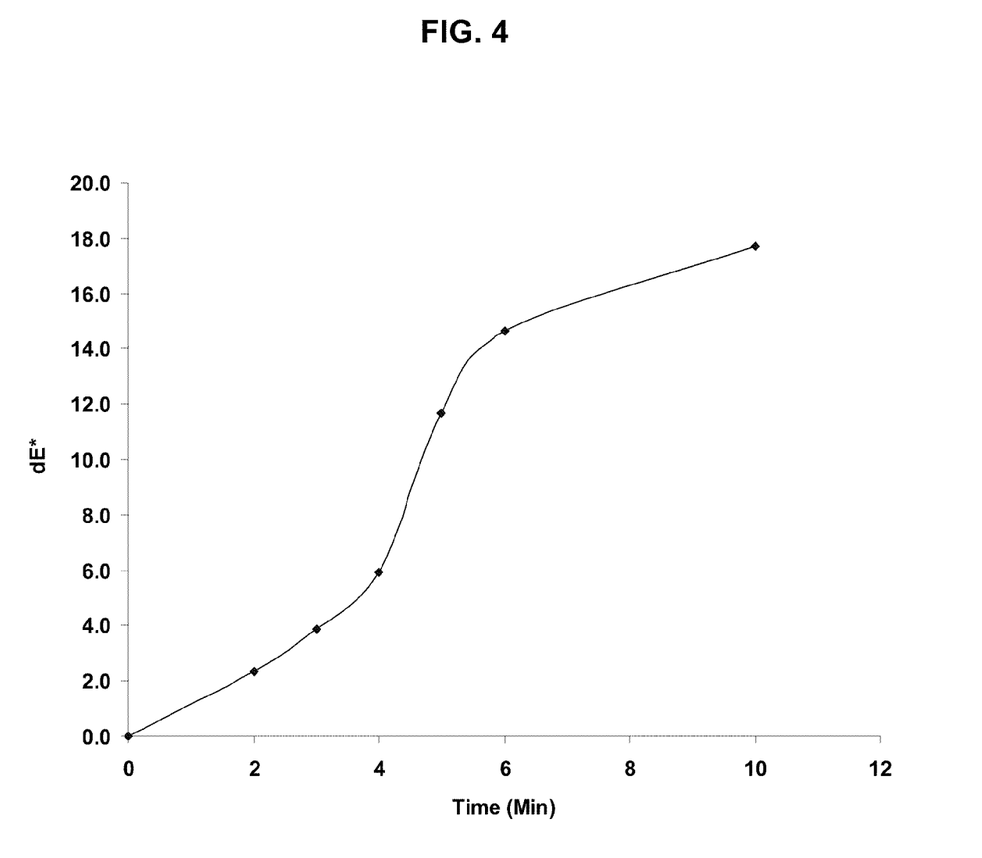
FIG. 4 is a graph of $\Delta E^*$ for Example 8, as a function of time at 75° C. in a no air-flow oven.

Photographic analysis. Examples 6-9 were drawn down over Kraft stock and air dried. The paper was cut into four sections and given the heat treatments prior to being taped back together for side-by-side analysis. A photograph of the papers and ink samples was then obtained after heat treatment and a line drawing representation of the photograph is provided in FIG. 3. Colors of the inks may be determined from the La*b* color values provided in Table 4. In FIG. 3, the heat treatments were as follows from the top of the figure: (1) 10 minutes at 55° C. as seen in the upper section; (2) no heat treatment; (3) 7 minutes at 75° C.; and (4) 30 seconds at 170° C. as seen in the lower section. All samples maintained their color at 55° C. and at no heat treatment. Examples 6 and 7 were observed to undergo significant color change to black under the 75° C. treatment, whereas the Examples 8 and 9 remain robust at the same temperature. The oven in which the samples were placed had forced air-flow. At 170° C. all samples turned black.

Example 11

ΔE* vs. time determination. Example 8 was drawn down over metal foil backed Kraft stock and air dried. The material was cut into strips and fixed in a manner so as not to touch a substrate and to prevent coiling. The strips were placed in a no air-flow chamber at 75° C. for various times. Strips were pulled at intervals and the color was measured using a handheld densitometer. The results are as follows: as illustrated above with respect to Example 8 and Table 4, the final color change, as expressed by ΔE*, is approximately 19. Example 13: At 60° C., there was no change in over 15 hours of exposure, i.e. ΔE*=0.

Example 12

As in Example 11, Example 8 was drawn down over metal foil backed Kraft stock and air dried. The material was cut into strips and fixed in a manner so as not to touch a substrate and to prevent coiling. The strips were placed in a no air-flow chamber at 60° C. for various times. Strips were pulled at intervals and the color was measured using a handheld densitometer. At 60° C., ΔE* was equal to zero after 15 hours of in the oven.

The present disclosure is not to be limited in terms of the particular embodiments described in this application. Many modifications and variations can be made without departing from its spirit and scope, as will be apparent to those skilled in the art. Functionally equivalent methods, formulations, and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of revealing exposure of a substrate to an environmental stimulus comprising:
    exposing said substrate to said environmental stimulus;
    wherein:
        said substrate comprises
            at least one indicia, wherein each of said at least one indicia comprises:
                a plurality of chromatically selective scattering particles having a particle size distribution as measured by (weight average diameter)/(number average diameter) of less than or equal to about 1.1, and
                a colorant;
            said at least one indicia exhibits a change in color in response to said environmental stimulus;
            said chromatically selective scattering particles comprise polymeric particles; and
            said polymeric particles have a glass transition temperature from about 20° C. to about 180° C.

2. The method of claim 1, wherein said environmental stimulus is heat, pressure, liquid, or vapor.

3. The method of claim 1, wherein said glass transition temperature is from about 40° C. to about 140° C.

4. The method of claim 1, wherein said colorant is a dye or pigment.

5. The method of claim 1, wherein said colorant is carbon black.

6. The method of claim 1, wherein said substrate is paper, paperboard, plastic film, or foil.

7. The method of claim 1, wherein said at least one indicia is a pattern, a logo, a picture, or text.

8. The method of claim 1, wherein said at least one indicia is configured to provide information regarding said environmental stimulus.

9. The method of claim 1, wherein said at least one indicia is at least a first indicia and a second indicia; and said chromatically selective scattering particles in said first indicia have a glass transition temperature that is different from a glass transition temperature of said chromatically selective scattering particles in said second indicia.

10. The method of claim 9 further comprising identifying a thermal history for a product comprising said substrate, based upon said observing a change in color.

11. The method of claim 9 further comprising identifying a counterfeit product comprising said substrate, based upon said observing a change in color.

12. The method of claim 1, wherein said chromatically selective scattering particles comprise an emulsion polymer or other types of polymer colloid.

13. The method of claim 1, wherein said weight average diameter of said chromatically selective scattering particles is from about 125 to about 700 nm.

14. The method of claim 1, wherein said chromatically selective scattering particles comprise polymeric particles polymerized from vinyl aromatic monomers, (meth)acrylic acid monomers, and (meth)acrylate monomers, or mixtures thereof.

15. The method of claim 1, wherein said chromatically selective scattering particles comprise polymeric particles polymerized from styrene, α-methylstyrene, butadiene, vinyl acetate, (meth)acrylic acid, 2-hydroxyethyl(meth)acrylate, 2-ethylhexyl acrylate or mixtures of any two or more thereof.

16. The method of claim 1, wherein said chromatically selective scattering particles comprise inorganic particles selected from the group consisting of silica particles, glass particles, and titanium dioxide particles.

17. The method of claim 1, wherein said chromatically selective scattering particles are a mixture of solid and hollow sphere particles.

18. The method of claim 1, wherein a ratio of refractive indices of said chromatically selective scattering particles and a surrounding medium is at least about 1.2.

* * * * *